United States Patent
Picornell Darder

(10) Patent No.: US 8,604,078 B2
(45) Date of Patent: Dec. 10, 2013

(54) FOSFOMYCIN PHARMACEUTICAL COMPOSITION

(76) Inventor: Carlos Picornell Darder, Madrid (ES)

( * ) Notice: Subject to any disclaimer, the term of this patent is extended or adjusted under 35 U.S.C. 154(b) by 0 days.

(21) Appl. No.: 13/423,443

(22) Filed: Mar. 19, 2012

(65) Prior Publication Data

US 2012/0258934 A1 Oct. 11, 2012

Related U.S. Application Data

(60) Provisional application No. 61/472,239, filed on Apr. 6, 2011.

(51) Int. Cl.
*A01N 43/20* (2006.01)
(52) U.S. Cl.
USPC ............... 514/475; 514/75; 514/99; 514/183; 514/449; 514/491

(58) Field of Classification Search
USPC ...................... 514/75, 99, 183, 449, 475, 491
See application file for complete search history.

(56) References Cited

U.S. PATENT DOCUMENTS

| | | | | |
|---|---|---|---|---|
| 4,716,153 A | * | 12/1987 | Morishita et al. | 514/30 |
| 7,303,755 B2 | * | 12/2007 | Rampoldi et al. | 424/400 |
| 2004/0253307 A1 | * | 12/2004 | Hague et al. | 424/464 |

* cited by examiner

*Primary Examiner* — Ali Soroush

(57) ABSTRACT

The present invention relates to a solid fosfomycin pharmaceutical composition stable in front the coloration, suitable for diabetics and not entailing gastrointestinal problems.

The pharmaceutical composition of this invention comprises fosfomycin trometamol, glycine, and optionally other excipients as sucralose, silice dioxide, polyvinylpyrrolidone and flavor; and is substantially free from sugars and sugar alcohols as sucrose, fructose, glucose, xylitol, mannitol, sorbitol or mixtures thereof.

12 Claims, No Drawings

FOSFOMYCIN PHARMACEUTICAL COMPOSITION

TECHNICAL FIELD

The present invention relates to a stable pharmaceutical composition for oral administration of the antibiotic fosfomycin.

BACKGROUND ART

Fosfomycin trometamol, which chemical name is mono(2-ammonium-2-hydroxymethyl-1,3-propanediol) (2R,cis)-(3-methyloxiranyl)phosphonate, is an antibiotic indicated in the prophylaxis and treatment of uncomplicated acute infections of the lower urinary tract.

There are some fosfomycin trometamol pharmaceutical compositions for oral administration disclosed in the state of the art.

The Spanish patent application ES495870 (Zambon, S.p.a.) describes a composition for oral administration in form of sachets containing fosfomycin trometamol, sodium carboxymethylcellulose, lactose, titanium dioxide, orange flavour and sucrose. The sucrose content in this composition, depending on the active substance dosage, changes between 56 and 76% as weight of the total composition.

Another Spanish patent application, ES 2020790 (Zambon Group, S.p.a.), discloses a granulated containing fosfomycin trometamol, saccharine, flavour and sucrose. The sucrose content in this composition comprises 28% as weight of the total composition.

The Spanish patent application ES2224869 (Zambon Group, S.p.a.) discloses the use of certain basic compounds to stabilize a fosfomycin trometamol pharmaceutical composition. Some compositions described in the examples also mention the use of between 16% and 22% of sucrose as weight of the total composition.

The Spanish patent application ES2244333 (Simbec Ibérica, S. L.) discloses a pharmaceutical preparation comprising fosfomycin trometamol, mannitol and/or xylitol and an artificial sweetening agent selected from the group including acesulfame, aspartame, saccharin, alitame and/or cyclamate. The mannitol and/or xylitol content comprises between 20-40% as weight of the total composition.

The presence of certain sugars such as sucrose, fructose or glucose in a fosfomycin trometamol pharmaceutical composition can arise in an undesirable colouration due to the reaction between the aldehyde groups of such sugars with the trometamol amine or any other primary amino group present in the composition. Furthermore, the presence of these sugars makes the obtained pharmaceutical composition not suitable for the administration to diabetic patients.

On the other hand, it is well known in the state of the art that pharmaceutical compositions comprising a sugar derivative such as a sugar alcohol, in particular xylitol, mannitol, sorbitol or mixtures thereof, can cause intestinal problems such as an undesirable laxative effect or abdominals gases.

DETAILED DESCRIPTION OF THE INVENTION

The present invention relates to a stable solid fosfomycin pharmaceutical composition for oral administration characterised by comprising fosfomycin trometamol, glycine, optionally other pharmaceutically acceptable excipients, and it is substantially free from sugars and sugar alcohols such as sucrose, fructose, glucose, xylitol, mannitol, sorbitol or mixtures thereof.

By the term "substantially free" it is understood that the sugar or sugar alcohol content is non-existent or so low that fosfomycin pharmaceutical composition of the invention still is stable from colouration, suitable for diabetics and no cause intestinal problems.

Glycine is a neutral amino acid with a pH value between 5.9 and 6.4 according to the European Pharmacopoeia 6.0. Glycine does not have any lateral chain; it is the unique amino acid without chiral centre.

This amino acid has a slight sweet taste that, different from other amino acids with bitter or acid taste, makes it suitable to be used as a diluent in an oral administration pharmaceutical composition. Furthermore, the absence of aldehyde groups on its structure avoids the coloration due to the Maillard reaction with amines making possible to obtain stable from coloration compositions. At the same time, a pharmaceutical composition comprising glycine does not represent any risk for diabetic patients because does not give any glycemic response, and no gastrointestinal problems such as an undesirable laxative effect or abdominal gases are arisen.

The amount of glycine can be easily determined by a person skilled in the art in order to get a fosfomycin trometamol solid oral pharmaceutical composition by known techniques usual in the state of the art. Generally, the amount of glycine presents in the fosfomycin pharmaceutical composition can comprise between 0.1 and 70% expressed by weight over the composition total weight. Preferably, the amount of glycine comprises between 20 and 50% as weight of the total composition.

Optionally, this fosfomycin trometamol pharmaceutical composition comprises one or more sweeteners to improve its palatability. Preferably, the sweetener is selected from the group including sucralose, acesulfame, aspartame, saccharine, alitame, cyclamate, neohesperidine dihydrochalcone, thaumatina and mixtures thereof.

More preferably, the sweetener used to improve the palatability of the pharmaceutical composition comprising fosfomycin trometamol and glycine is sucralose. This compound is between 300 and 1000 times sweeter than sucrose, does not have the aftertaste characteristic of other artificial sweeteners, is not absorbed by the organism and does not present toxicity problems.

The addition of sucralose to the pharmaceutical composition allows obtain a more pleasant taste using only a small quantity of such a sweetener. The fosfomycin trometamol and glycine pharmaceutical composition of this invention can comprise between 0.0 and 5.0% of sucralose, preferably between 1.0 and 2.0% as weight of the total composition.

In a preferred embodiment, the fosfomycin pharmaceutical composition is presented in form of powder or granulates for solution. More preferably the powder or granulates for solution are contained in single dosages sachets for solution.

Optionally, the fosfomycin pharmaceutical composition further comprises one or more of other pharmaceutical acceptable excipients usual in the pharmaceutical industry to obtain oral administration solid compositions, in particular to obtain pharmaceutical compositions in form of powder or granulate for solution.

Preferably these excipients are selected from the group including glidants such as calcium silicate, magnesium silicate, silicon dioxide, magnesium stearate, magnesium oxide, talc, cellulose, starch or mixtures thereof; binders such as microcrystalline cellulose, pregelatinized starch, copovidone, polyvinylpyrrolidone (povidone), hydroxypropylmethyl cellulose, hydroxypropyl cellulose, hydrogenated vegetable oil or mixtures thereof; and/or flavours such as orange, tangerine, lemon, raspberry, strawberry or coconut.

More preferably, the fosmomycin trometamol and glycine pharmaceutical composition further comprises sucralose as sweetener, silicon dioxide as glidant, polyvinylpyrrolidone as binder and lemon flavour.

The pharmaceutical composition of this invention generally contains between 1.9 and 7.5 g of fosfomycin trometamol, corresponding to 1.0 and 4.0 g of fosfomycin expressed as free acid. Preferably, the composition contains between 3.8 g and 5.6 g of fosfomycin trometamol, corresponding to 2.0 and 3.0 g of fosfomycin expressed as free acid.

The drug substance amounts previously mentioned corresponds to between 30% and 99.9% by weight over the composition total weight. Preferably, the content of fosfomycin trometamol represents between 50% and 80% by weight over the composition total weight.

The fosfomycin stable solid pharmaceutical composition for oral administration of this invention can be used for the manufacture of a medicament for the treatment or profilaxis of uncomplicated acute infections of the lower urinary tract.

Furthermore, the fosfomycin stable solid pharmaceutical composition for oral administration of this invention can be used for the treatment or profilaxis of uncomplicated acute infections of the lower urinary tract.

The fosfomycin pharmaceutical composition to this invention can be obtained by methods widely known by the person skilled in the art, in particular by mixing and/or granulation methods.

EXAMPLE

Powder or Granulate for Solution

The components are homogeneously mixed and, optionally, granulated by known techniques usual in the state of the art. The solid obtained is dosed in sachets containing the quantity equivalent to 2.0 g or 3.0 g of fosfomycin in acid form.

| | |
|---|---|
| Fosfomycin trometamol | 63% |
| Glycine | 32% |
| Sucralose | 1.3% |
| Lemon flavour | 1.4% |
| Silicon dioxide | 0.1% |
| Polyvinylpyrrolidone | 2.2% |
| Total | 100% |

The invention claimed is:

1. A stable solid fosfomycin pharmaceutical composition for oral administration characterized by comprising
    a) fosfomycin trometamol,
    b) glycine and
    c) optionally other pharmaceutical acceptable excipients, and it is substantially free from sugars and sugar alcohols.

2. The pharmaceutical composition according to claim 1, characterized by further comprising a pharmaceutically acceptable sweetener.

3. The pharmaceutical composition according to claim 2, characterized in that the sweetener is selected from the group including sucralose, acesulfame, aspartame, saccharine, alitame, cyclamate, neohesperidine dihydrochalcone, thaumatina and mixture thereof.

4. The pharmaceutical composition according to claim 3, characterised in that the sweetener is sucralose.

5. The pharmaceutical composition according to claim 1, characterised by comprising other pharmaceutically acceptable excipients.

6. The pharmaceutical composition according to claim 1, characterised by comprising, expressed as weight of the total composition:
    a) between 30% and 99.9% fosfomycin trometamol,
    b) between 0.1 and 70% glycine, and
    c) optionally other pharmaceutically acceptable excipients in quantity enough to complete the 100% of the composition total weight.

7. The pharmaceutical composition according to claim 6, characterised by comprising, expressed as weight of the total composition:
    a) about 63% fosfomycin trometamol,
    b) about 32% glycine, and
    c) optionally other pharmaceutically acceptable excipients in quantity enough to complete the 100% of the composition total weight.

8. The pharmaceutical composition according to claim 6, characterised by comprising, expressed as weight of the total composition:
    a) between 30% and 99.9% fosfomycin trometamol,
    b) between 0.1 and 70% glycine,
    c) between 0.0 and 5.0% sweetener, and
    d) optionally other pharmaceutically acceptable excipients in quantity enough to complete the 100% of the composition total weight.

9. The pharmaceutical composition according to claim 7, characterised by comprising, expressed as weight of the total composition:
    a) about 63% fosfomycin trometamol,
    b) about 32% glycine,
    c) about 1.3% sucralose,
    d) about 0.1% silicon dioxide,
    e) about 2.2% polyvinylpyrrolidone, and
    f) about 1.4% lemon flavour.

10. The pharmaceutical composition according to claim 8, characterised in being powder or granulate for solution.

11. The pharmaceutical composition according to claim 10, characterised in that the powder or granulate for solution is soluble in water.

12. A method of treatment and/or prophylaxis of a mammal suffering from or being susceptible to uncomplicated acute infections of the lower urinary tract, said method comprising the administration to said mammal, of the fosfomycin stable solid pharmaceutical composition for oral administration as defined in claim 1.

* * * * *